US009636680B2

(12) United States Patent
Fattinger et al.

(10) Patent No.: US 9,636,680 B2
(45) Date of Patent: May 2, 2017

(54) SAMPLE HANDLING SYSTEM

(71) Applicant: F. Hoffmann-La Roche AG, Basel (CH)

(72) Inventors: Christof Fattinger, Blauen (CH); Tom Kissling, Riehen (CH); Thomas Zumstein, Weil am Rhein (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 14/376,123

(22) PCT Filed: Feb. 1, 2013

(86) PCT No.: PCT/EP2013/052033
§ 371 (c)(1),
(2) Date: Jul. 31, 2014

(87) PCT Pub. No.: WO2013/113874
PCT Pub. Date: Aug. 8, 2013

(65) Prior Publication Data
US 2015/0017078 A1  Jan. 15, 2015

(30) Foreign Application Priority Data

Feb. 3, 2012 (EP) .................................. 12153770

(51) Int. Cl.
*B01L 9/06* (2006.01)
*B01L 3/00* (2006.01)
(Continued)

(52) U.S. Cl.
CPC ............... *B01L 9/06* (2013.01); *B01L 3/5082* (2013.01); *B01L 3/5085* (2013.01);
(Continued)

(58) Field of Classification Search
CPC .......... B01L 3/508; B01L 9/06; B01L 3/5082; B01L 3/50855; B01L 3/5085; G01N 35/026
(Continued)

(56) References Cited

U.S. PATENT DOCUMENTS 3,643,812 A  2/1972  Mander et al.
4,284,603 A  8/1981  Korom
(Continued)

FOREIGN PATENT DOCUMENTS

DE  9002496 U1  5/1990
EP  0365827 A2  5/1990
(Continued)

OTHER PUBLICATIONS

Fattinger, Christof et al., "High-Density Plates, Microarrays, Microfluidics," *Exploiting Chemical Diversity for Drug Discovery*. Royal Society of Chemistry, 2006, Chapt. 9, pp. 203-232.
(Continued)

*Primary Examiner* — P. Kathryn Wright
(74) *Attorney, Agent, or Firm* — Mintz Levin Cohn Ferris Glovsky and Popeo, P.C.

(57) ABSTRACT

Sample handling system for handling samples contained in tubes (4), each tube (4) having a hollow body, a closed bottom and an open top for accessing the sample contained in the tube (4). The system comprises a micro-plate (1) comprising at least one grid insert (2) having a plurality of compartments. Each compartment comprises one or more side walls laterally confining a through-hole for receiving a said tube (4). The through-hole has a top opening and a bottom opening and extends between the top opening and the bottom opening. A frame (3) to which the at least one separate grid insert (2) is to be attached to form the micro-plate (1). The frame (3) laterally confines a through-opening
(Continued)

which is dimensioned to allow for accessing each compartment (21) of the attached at least one grid insert (2) from above and from below. This allows for moving such tube (4) into and out of each compartment (21) through each of the top opening (202) and the bottom opening (203) of the through-hole (201).

14 Claims, 7 Drawing Sheets

(51) Int. Cl.
    *B01J 19/00*     (2006.01)
    *G01N 35/02*     (2006.01)
    *G01N 35/04*     (2006.01)

(52) U.S. Cl.
    CPC ........ *B01L 3/50855* (2013.01); *G01N 35/026* (2013.01); *B01L 2200/02* (2013.01); *B01L 2200/025* (2013.01); *B01L 2200/028* (2013.01); *B01L 2200/0689* (2013.01); *B01L 2300/021* (2013.01); *B01L 2300/044* (2013.01); *B01L 2300/0609* (2013.01); *B01L 2300/0829* (2013.01); *G01N 2035/041* (2013.01); *G01N 2035/0405* (2013.01)

(58) Field of Classification Search
    USPC ......................................... 422/104, 554, 549
    See application file for complete search history.

(56) References Cited

U.S. PATENT DOCUMENTS

| | | | | |
|---|---|---|---|---|
| 4,433,815 | A | * | 2/1984 | D'Agnolo ............... B65H 75/18 138/155 |
| 5,456,360 | A | | 10/1995 | Griffin |
| 6,098,819 | A | * | 8/2000 | Link ....................... B01L 9/543 206/504 |
| 2001/0002986 | A1 | * | 6/2001 | Fattinger .............. B01J 19/0046 422/562 |
| 2003/0129095 | A1 | | 7/2003 | Farina et al. |
| 2007/0031296 | A1 | | 2/2007 | Coulling et al. |
| 2007/0116613 | A1 | * | 5/2007 | Elsener ............... B01L 3/50255 422/400 |
| 2007/0172396 | A1 | * | 7/2007 | Neeper ............ G01N 35/00732 422/400 |
| 2008/0164210 | A1 | * | 7/2008 | DeMarco ....................... 210/656 |
| 2008/0206112 | A1 | * | 8/2008 | Fu ............................. B01L 9/06 422/400 |
| 2011/0158777 | A1 | | 6/2011 | Nishii et al. |
| 2012/0094388 | A1 | | 4/2012 | Belz et al. |

FOREIGN PATENT DOCUMENTS

| | | |
|---|---|---|
| EP | 0904841 A2 | 3/1999 |
| JP | 11-160325 | 6/1999 |
| JP | 2004-259178 | 9/2004 |
| JP | 2005-514633 | 5/2005 |
| JP | 2006-214919 | 8/2006 |
| JP | 2007-37549 | 2/2007 |
| JP | 2007-171169 | 7/2007 |
| JP | 2011-137640 | 7/2011 |
| JP | 2011-227076 | 11/2011 |
| WO | WO-2004060534 A1 | 7/2004 |
| WO | WO-2007001163 A1 | 5/2007 |
| WO | WO-2008006746 A2 | 1/2008 |

OTHER PUBLICATIONS

English abstract of JP 2007-37549 dated Feb. 15, 2007.
English abstract of JP 2007-171169 dated Jul. 5, 2007.
English abstract of JP 2005-514633 dated May 19, 2005.
English abstract of JP 2011-227076 dated Nov. 10, 2011.
English abstract of JP 2004-259178 dated Sep. 16, 2004.
English abstract of JP 11-160325 dated Jun. 18, 1999.
English abstract of JP 2006-214919 dated Aug. 17, 2006.
English abstract of JP 2011-137640 dated Jul. 14, 2011.

* cited by examiner

SAMPLE HANDLING SYSTEM

CROSS-REFERENCE TO RELATED APPLICATIONS

This application is a national phase of International Application No. PCT/EP2013/052033, filed on Feb. 1, 2013, which claims priority to European Patent Application No. 12153770.8, filed on Feb. 3, 2012. The contents of all of these applications are expressly incorporated herein by reference in their entireties.

FIELD

The present invention relates to a sample handling system according to the independent claim.

BACKGROUND

It is well-known to use sample handling systems to store and retrieve high numbers of samples in automated sample libraries. A sample may be, for example, an aliquoted and/or diluted chemical or biochemical compound solved in dimethyl-sulfoxide (DMSO), or a biological sample, and the libraries of these samples are contained in a frozen state in a humidity controlled cold-room in freezers at −20° C. or −80° C. The samples retrieved from the cold room can then—after thawing—directly be used for high-throughput screening (HTS) of substances for their activity on specific biological targets of interest, or for biological studies or assays, as this may be performed in the drug discovery process.

A compound handling system of this type which is capable of handling a multiplicity of chemical or biological samples is known from U.S. Pat. No. 6,827,907 B2 and comprises a single piece storage plate which has a grid-like arrangement of separation walls defining 384 rectangular storage compartments. The 384 storage compartments are configured and dimensioned to hold a corresponding number of micro-tubes. The storage compartments are open to the top and the bottom to form through holes for receiving the micro-tubes. After filling the samples into the micro-tubes all micro-tubes arranged in the compartments of the storage plate are covered with a sealing foil which is then sealed to the upper edges of the micro-tubes. Thereafter, the foil is punched around the micro-tubes so as to remove those parts of the foil arranged in the space between the micro-tubes to make all 384 micro-tubes individually accessible. In order to allow retrieval and processing of individually composed compound subsets from the large sample libraries, the respective samples are pushed from the storage compartments of the respective storage plates through the open bottom thereof into the compartments of a delivery plate arranged beneath the storage plate, so that the delivery plate then comprises the respective individually composed compound subset.

Taking into consideration that such compound libraries may comprise up to several millions of individual samples, known sample handling systems suffer from the disadvantage that due to the corresponding large number of storage plates much storage space is required in the cold room. Due to standardization of micro-plates, the outer dimensions of the storage plates cannot be changed. Accordingly, it is not possible to increase the number of storage compartments on the micro-plates through an increase of the outer dimensions of the micro-plates. Increasing the number of individual compartments on micro-plates with standardized outer dimensions by simply reducing the dimensions of the individual compartments of the grid may lead to compartments bounded by side walls having a wall thickness which may be too small to provide a mechanically stable support for the tubes in the micro-plate. For example, if the capacity of the conventional tube micro-plates having 384 compartments (16×24) would have to be increased, a micro-plate having increased capacity while maintaining the area where the compartments for receiving the tubes are arranged and while maintaining the arrangement of the compartments would need 1536 compartments ([2×16]×[2×24]=1536). This would result in a tube micro-plate having too small a wall thickness to provide adequate support for the tubes to be received in the compartments and for the means for punching the tubes through the open bottom of the compartments of the storage plate into corresponding compartments of a delivery plate (see further above).

Another problem connected with "downsizing" of the individual compartments of micro-plates with standardized outer dimensions is related to the manufacturing of such micro-plates, since micro-plates are typically injection-molded from a suitable molding material (e.g. an injection-moldable plastic). The reduced thickness of the side walls of the compartments can then no longer be reliably manufactured by injection-molding, since the injection-moldable material is not capable of being reliably injected into the very small spaces of the mold that correspond to the side walls of reduced wall thickness (of a 1536 compartments tube micro-plate). On the other hand, manufacturing the micro-plates by injection-molding is important as injection-molding is a manufacturing technique which is very reliable and cost-effective with respect to mass-manufacturing. In this respect, it has to be taken into consideration that high numbers of micro-plates are needed for the compound libraries.

SUMMARY

Accordingly, it is an object of the invention to provide a sample handling system which overcomes or at least reduces the afore-mentioned disadvantages of prior art systems. In addition, the sample handling system shall be suitable for conventional manufacturing using injection-molding techniques.

In accordance with the invention, this object is achieved by a sample handling system as it is characterized by the features of the independent claim. Advantageous aspects of the sample handling system according to the invention are the subject of the dependent claims.

In particular, the invention relates to a sample handling system for handling samples contained in tubes, each tube having a hollow body, a closed bottom and an open top for accessing the sample contained in the tube. The sample handling system includes a micro-plate comprising at least one separate grid insert having a plurality of compartments. Each compartment comprises one or more side walls laterally confining a through-hole. The through-hole has a top opening and a bottom opening and extends between the top opening and the bottom opening. The micro-plate further comprises a frame to which the at least one separate grid insert is to be attached to form the micro-plate. The frame laterally confines a through-opening which is dimensioned to allow for accessing each compartment of the attached at least one grid insert from above and from below, and to allow for moving such tube into and out of each compartment through each of the top opening and the bottom opening of the through-hole.

The sample handling system accordingly comprises a separate grid insert which can be attached to (and preferably also detached from) the frame. This has a plurality of advantages. A higher storage capacity within a cold room comprising freezers of a given size can be achieved because the effective storage volume required for the same number of tubes is reduced since storing of the grid inserts with the tubes only, that is to say without the frame, requires less space. Or to say it in other words, the number of samples which can be stored in a cold room comprising freezers of a given size is increased.

Each sample tube is stored in a grid insert in an individual compartment. Each compartment has one or more side walls laterally confining a through-hole. The through-hole has a top opening and a bottom opening and extends between the top opening and the bottom opening. Depending on the length of the tube, the tube is received either completely in the compartment or extends out of the compartment through at least one of the top opening or the bottom opening. The through-hole preferably has a constant cross-section along its length and in any event allows for movement of the tube along the compartment and out of the compartment through the top opening as well as through the bottom opening of the through-hole. Preferably, the frame encloses the attached at least one grid insert only laterally. For example, inner walls of the frame confine a single through-opening through which each compartment of the attached grid insert is accessible. Preferably, the single through-opening is dimensioned so as to have a shape and size allowing for accommodating at least some of the outer walls of the grid insert. In particular, the frame which encloses one or more such separate grid inserts at the side walls only, allows for accessing the at least one or more grid inserts from above and from below. Thus, the tubes can be moved into and out of each compartment through the top opening of the respective compartment and through the bottom opening of the respective compartment. For example, access to the one or more grid inserts includes arranging compartments of a further grid insert (or further micro-plate) above or below the one grid insert so as to align the compartments of the further grid insert arranged above or below the one grid insert with those compartments of the one grid insert. The tubes can then be punched from a compartment of the one grid insert into the compartments of the further grid insert (or a destination micro-plate) in a transfer process for selectively retrieving samples contained in tubes. Accessibility of the compartments of a grid insert from above and below permits the use of punching means punching the tubes out of the individual compartments of the grid insert or of gripping means for gripping and holding the tubes. The frame of the micro-plate can in principle be of any contour, but in a preferred embodiment the frame has a lateral contour having the dimensions of a standard micro-plate. The dimensions of such standard micro-plates are preferably ANSI/SBS-compliant (American National Standards Institute/Society for Biomolecular Screening) and are well-known to those skilled in the art (ANSI/SBS 1-2004). The standard dimensions of such standard micro-plates are 127.76 mm×85.48 mm (about 5.03 inches×3.37 inches). Micro-plates having such contour are advantageous since they allow handling of the micro-plates with equipment available for handling standard micro-plates. The separate grid insert or grid inserts can be attached to the frame permanently or non-permanently. A permanent attachment of the separate grid insert to the frame may be of advantage if both the frame and the grid insert are to be disposed of after use, so that there is no need to detach the grid insert from the frame after use. A non-permanent attachment of the separate grid-like insert to the frame allows detachment of the grid insert from the frame. The possibility of detaching the grid insert from the frame allows, for example, the transfer of the separate grid insert from one frame into another frame during the sample handling process, or the transfer of the grid insert back into the freezer in the cold room. Typically, the samples are contained in tubes in quantities of 20 µl to 100 µl, in a particular example in quantities of 22 µl, 26 µl or 80 µl. "Handling of samples" includes any type of handling but in particular includes aliquoting of a sample contained in a tube, sealing of tubes, retrieving tubes from a freezer in a cold room and transferring tubes back into the freezer, transferring tubes from a storage plate into a delivery plate and deliver tubes arranged in the delivery plate. A further advantage is achieved by the separate production of the frame and the grid insert. While the frame is formed from elements having a higher volume (e.g. the comparatively massive side walls) the elements of the grid are of small volume (e.g. the comparatively thin side walls confining the compartment). When using injection molding techniques, the quality of the moldings produced can be improved if the elements of a molding to be produced are of similar volume. Thus, by separating the grid insert and the frame, the quality of these injection-molded parts can be improved.

In accordance with one aspect of the sample handling system according to the invention, the frame or the separate grid insert or both comprise fastening elements fixedly attaching the grid insert to the frame. While generally attachment of the separate grid insert to the frame can be achieved with the aid of separate fastening elements, for example locking elements such brackets or clips, preferably the fastening elements are provided on the separate grid insert or the frame rather than being separate elements. Fastening can be achieved by means of a form locking engagement of the grid insert and the frame (or of parts thereof) or can be achieved through a frictional fit. Alternatively or additionally, specific fastening elements can be formed on the frame and the grid insert such that the grid insert is attached to the frame semi-permanently or permanently. For example, the fastening elements can form a snap-fit or a clamp-fit to form a detachable connection between grid insert and frame.

In accordance with a further aspect of the sample handling system according to the invention, the fastening elements for fixedly attaching the separate grid insert to the frame comprise one or more protrusions arranged on a resilient portion of the inner wall of the frame and a one or more recesses arranged on a portion of the outer wall of the grid insert. The one or more protrusions lockingly engage with the one or more recesses when the grid insert is inserted into the frame from below. The number of protrusions which corresponds to the number of recesses may for example be eight so that two protrusions are arranged on each side on the inner wall of the frame and two corresponding recesses are formed on each side on the outer wall of the grid insert to achieve a secure fit of the grid insert within the frame. For engagement of the protrusion into the recess, the resilient portion of the inner wall of the frame allows to elastically deform so as to move the protrusion from a first position in which the grid insert can be inserted into the frame to a second position in which the protrusion engages into the recess and locks the grid insert to the frame. Inserting the grid insert into the frame from below in particular allows locking of a single grid insert as well as of a stack of grid inserts in a similar manner, as will be described further below.

In accordance with a still further aspect of the sample handling system according to the invention, the separate grid insert comprises stacking elements for connecting to the grid insert at least one further separate grid insert to form a stack of connected grid inserts which are arranged one above the other. The stacking elements comprise at least one resilient locking member extending downwardly beyond the respective grid insert and at least one notch arranged to lockingly receive the resilient locking member of the above-arranged grid insert of the stack. To further increase the storage capacity of the sample handling system according to the invention, more than one grid insert can be stored in a stack of grid inserts. This allows the storage of a still higher number of tubes in a micro-plate with two or more tubes being stored in a manner longitudinally aligned one above the other in the micro-plate which then comprises the stack of grid inserts attached to the frame. The grid inserts stacked in such manner are of reduced height compared to the grids of standard micro-plates so as to be suitable to accommodate tubes of reduced length. This allows storage of a higher number of smaller tubes in a given storage space compared to the storage of state of the art tubes in standard micro-plates. For example, if a standard grid of a micro-plate comprises 96 compartments, the stack comprises an integer multiple To arrange the grid inserts in a stack, the grid inserts are successively connected such as to be arranged one above the other in a manner such that each subsequent grid insert is connected to that grid insert which has been attached to the stack before. To form such connection, the stacking elements of the respective grid insert comprise a resilient locking member extending downwardly beyond the respective grid insert to be capable of being locked in a notch of the grid insert arranged immediately below.

Advantageously, the stack of grid inserts is attached to the frame by the fastening elements of the frame and of the uppermost grid insert of the stack. The use of the fastening elements of the uppermost grid insert of the stack allows attaching the stack in the same manner as a single grid insert is attached to the frame so that no additional fastening elements are required to attach the stack of grid inserts to the frame. A further advantage is related to the number of grid inserts which form the stack. The additional grid inserts can be attached to the frame by simply attaching them to the lowermost grid insert of the stack, the uppermost grid insert of which is already attached to the frame. Accordingly, this attachment of further grid inserts from below can be performed without the need to change the attachment of the uppermost grid insert of the stack which is the only grid insert of the stack that is attached to the frame.

In this manner, the compartments of the grid inserts of the stack are mated to form joint through-holes along which a tube is movable. The stacked grid inserts are arranged one above the other such that the respective side walls of each compartment are aligned to allow a tube to be reversibly transferred from one compartment into the mating compartment of the adjacent grid insert. Such transfer can be carried out by simply pushing the tube along the joint through-hole by a suitable punching means. In a first example, all tubes in one joint through-hole contain identical samples. This allows storage of multiple tubes with the same content in a joint through-hole of a suitable length. An advantage thereof is that no destacking of grid inserts is necessary in case a predetermined number of tubes of the same type of sample must be retrieved from the storage. It is then simply possible to punch the tubes sequentially out of the joint through-hole and to pick the respective lowermost or uppermost tube which is pushed out of the joint through-hole (depending on whether punching is performed from above or from below), since all tubes of the joint through-hole have the same content. Also, no destacking of grid inserts is necessary in case a specific tube arranged in a specific grid insert in the stack is needed (cherry-picking). Rather, it is then possible to punch those tubes arranged above or below the specific tube having the desired content (depending on whether punching is performed from above or below) into a gripping means or a buffer plate until that tube having the desired content is punched out of the joint through-hole. Then the desired tube is picked and placed into a destination standard micro-plate, for example, which can then be further processed. Those tubes arranged in the gripping means or in the buffer plate can then be placed back into the joint through-hole. In any event, even if it is desired to pick a tube having a particular content and this tube is arranged at any position in the stack it is thus efficiently possible to retrieve this tube from the stack without the need of destacking the grid inserts.

In accordance with another aspect of the sample handling system according to the invention, the frame has an insertion height greater than or equal to the overall height of the stack. While the height of the frame is in generally not restricted it may be the height of a standard micro-plate. Advantageously, the height is chosen so as to be capable of accommodating a stack of a predetermined number of grid inserts. The grid inserts are then attached to the frame in a manner such that when the frame is set down onto a flat surface the underside of the lowermost grid insert is not in contact with this surface so that the tubes contained in the compartment of the lowermost grid insert are properly protected.

According to a further aspect of the sample handling system according to the invention, the grid insert comprises a machine-readable identification label for identifying the grid insert and the tubes received therein. Because the micro-plate according to the invention has one or more separate grid inserts and because generally the grid inserts can be attached to the frame in any desired order, the grid inserts must be identified individually, for example by a machine-readable identification label. A machine-readable identification label allows handling of the plates by a robot comprising a suitable reading unit which is capable of identifying the grid insert or inserts. The information contained in the identification label can thus be easily retrieved and processed in a processing unit which also has access to a database comprising information as to what samples are contained in the compartments of the individual grid inserts, so that the location of every individual tube in each grid insert is known at any time, so that it is always possible to pick a particular individual tube from that grid insert in which that particular tube is actually stored.

In accordance with yet a further aspect of the sample handling system according to the invention, the frame has a recessed section arranged at a position corresponding to the position of the identification label of the grid insert attached thereto. The recessed section is preferably arranged in a side wall of the frame. The position of the recessed section generally corresponds to the position or positions where the identification labels are provided on the respective grid inserts.

In accordance with yet another aspect of the sample handling system according to the invention, each compartment comprises a circumferential projection extending inwardly from the one or more side walls confining the through-hole. The circumferential projection forms an abutment element for a complementary formed tube preventing the tube from being moved further into the through-hole of the respective compartment. The circumferential projection can extend inwardly from a single side wall (as this is the case, for example, for circular shaped through-holes) or may extend inwardly from more than one side walls (as this is the case, for example, for rectangular shaped through-holes).

As has already been indicated, in accordance with a further aspect of the sample handling system according to the invention the system may further comprise tubes, each tube having an abutment portion at the lower end of the tube and a circumferential rim at the open top of the tube. The abutment portion at the lower end of the tube is capable of abutting against the circumferential rim of a tube arranged underneath (in case of stacked grid inserts). The abutment portion can be realized through a geometry comprising multiple surfaces to abut against the circumferential rim of the tube arranged underneath. The tubes generally can be of any known type with respect to its size and outer shape. Such tube generally has a hollow body with a closed bottom to form a cavity in which the sample is contained. The open top can be closed by a lid foil which is to be destroyed or removed for accessing the sample contained in the tube.

In accordance with a further aspect of the sample handling system according to the invention, the tube on its outer wall comprises a circumferentially running groove having a width extending in the axial direction and a circumferentially extending ledge which forms the upper boundary of the circumferentially running groove. In a storage position of the tube the ledge abuts against the circumferential projection extending inwardly from the one or more side walls of the respective compartment of the grid insert, and in a sealing position of the tube the circumferential projection extends inwardly from the one or more side walls of the compartment of the grid insert into the groove provided on the outer wall of the tube at a position spaced from the ledge. This is particularly advantageous when the tubes containing the samples are sealed by sealing a foil sheet to the upper ends of the tubes while the tubes are arranged in the sealing position in which the upper ends of the tubes project upwardly above the upper end of the grid insert. The tubes can be supported and held in the sealing position by a suitable means such as a matrix of cylindrical elements projecting from below into the individual compartments of a grid insert. After sealing the foil sheet to the upper ends of the tubes, the foil is punched around the tubes thus creating individually sealed tubes. Subsequently, the tubes are pushed back into the compartments of the grid insert into the storage position in which the ledge abuts against the circumferential projection projecting inwardly from the respective compartment. The micro-plates as a whole or the individual grid inserts only carrying the individually sealed tubes in the storage position can then be transported to the humidity controlled cold-room where the compound libraries are long-term stored.

In accordance with yet a further aspect of the sample handling system according to the invention, the system further comprises a storage tray comprising a plurality of storage compartments, each storage compartment being capable of accommodating at least one grid insert. The micro-plate comprising a frame which is separable from a grid insert has the advantage that the grid insert can be stored without frame. This advantage is made use of when storing the grid insert only in the tray. The tray containing the frameless grid inserts increases the storage capacity, since the outer dimensions of the grid insert only are smaller than that of a micro-plate comprising a frame and the grid insert. Thus, the size of the storage compartments of the tray can be adapted to the size of the grid inserts, so that a greater number of grid inserts can be stored in a tray of a given length and height. For example, ten grid inserts can be stored in a tray of a given size instead of eight standard microplates. Different possibilities are available as regards the arrangement of the storage compartments in the tray. In a first example, the storage compartments are arranged in the longitudinal direction (pull-out direction) of the tray one after the other in a single row. Alternatively, the storage compartments can be arranged in parallel rows side by side. The arrangement in parallel rows is of advantage insofar as the overall storage capacity of each single tray is increased. Furthermore, the retrieving speed is increased since the time for pulling out the trays can be shortened.

In accordance with a further aspect of the sample system according to the invention, the storage compartments of the storage tray have a depth such that they are capable of accommodating a stack of grid inserts. This measure further increases the storage capacity, since in each compartment of the storage tray a stack of grid inserts can be stored. Accordingly, due to the increased stock that can be kept in the cold room the time intervals can be increased after which a refill operation must be performed so as to provide an adequate stock of samples in the cold room.

In accordance with a still further aspect of the sample handling system according to the invention, the tray comprises position markers thereon at the locations of the storage compartments for indicating the position of the grid insert or the stack of grid inserts in the respective storage compartment. Such position markers can be of any type like a recess, a protrusion or a label which is indicative of the position of the grid insert or stack of grid inserts in the respective compartments of the tray.

DETAILED DESCRIPTION OF THE FIGURES

Further advantageous aspects of the sample handling system according to the invention become apparent from the following description of embodiments of the invention with reference to the accompanying drawings in which.

DETAILED DESCRIPTION

Figure 1:
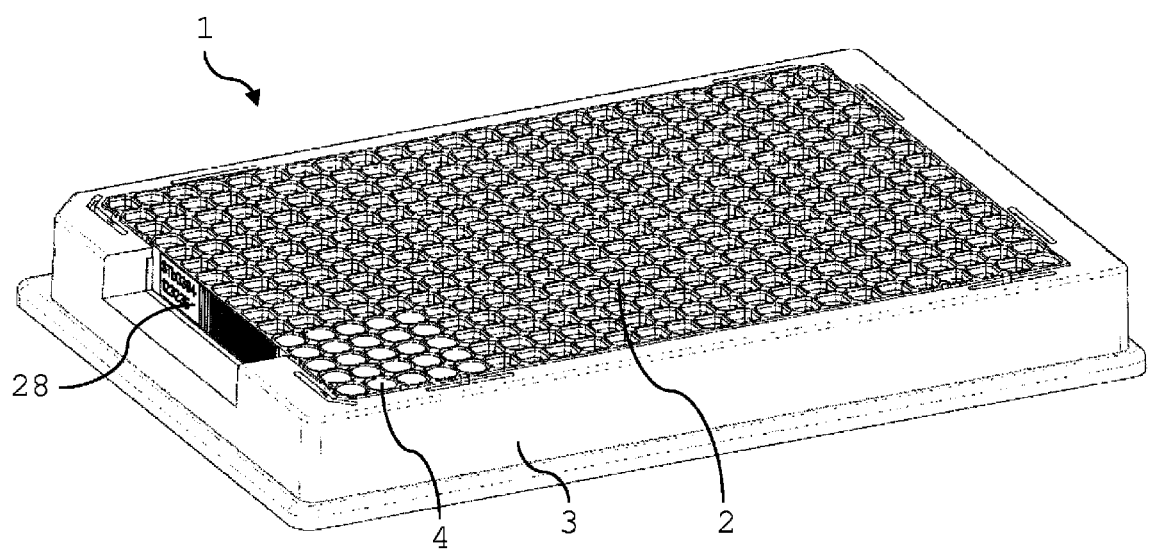
FIG. 1 shows perspective view of a micro-plate of a sample handling system according to the invention in the assembled state.
Figure 2:
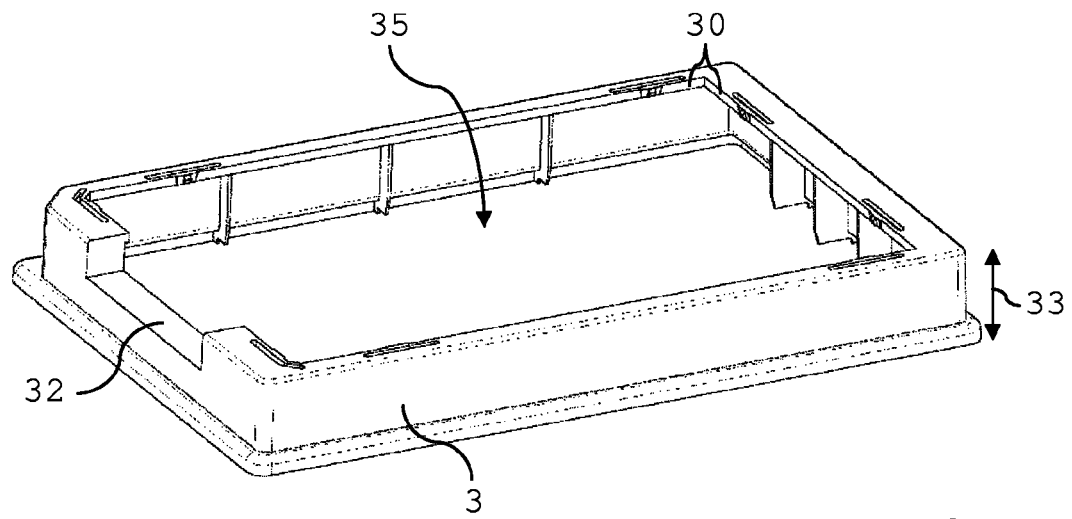
FIG. 2 shows a plan view of the frame of the micro-plate of FIG. 1.
Figure 3:
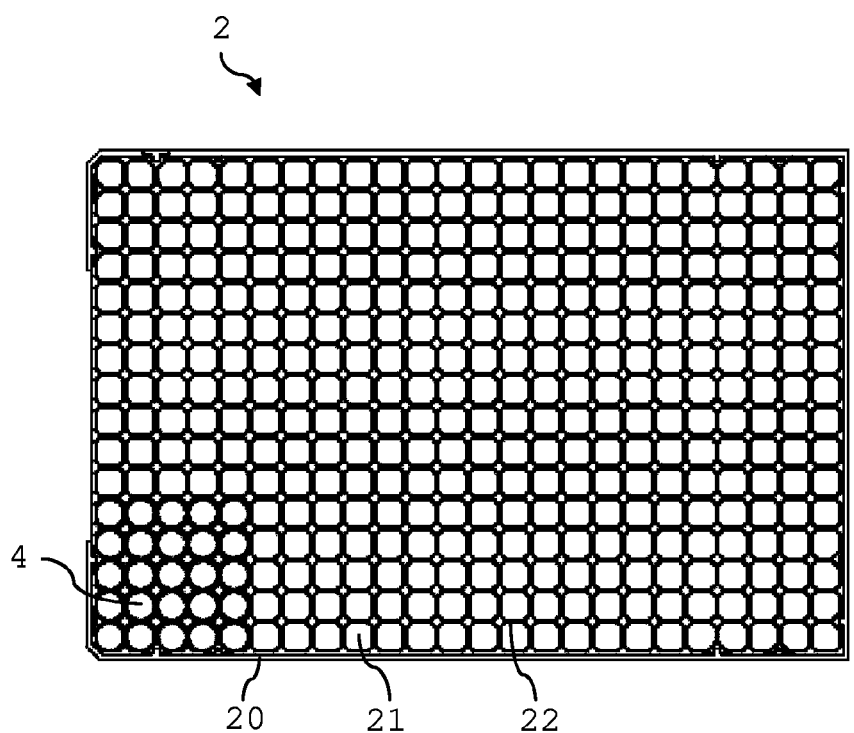
FIG. 3 shows a plan view of the grid insert of the micro-plate of FIG. 1.

FIG. 1 shows a micro-plate 1 of a sample handling system according to one embodiment of the invention. Micro-plate 1 comprises a frame 3 and a separate grid insert 2 which is already attached to the frame 3. FIG. 2 shows the separate frame 3 and FIG. 3 shows the separate grid 2 of the micro-plate 1 of FIG. 1 and, for the sake of clarity, these drawings are described together in the following. Frame 3 defines the overall lateral contour of micro-plate 1. The outer contour of frame 3 is of rectangular shape and has the dimensions of a standard micro-plate 1. This standard outer contour allows handling of the micro-plate 1 using standard equipment designed for the handling of standard micro-plates. The insertion height 33 of frame 3 is generally not limited to specific dimensions but is correlated to the number of grid inserts 2 to be accommodated in frame 3. In the present embodiment, insertion height 33 of frame 3 is slightly greater than or equal to the overall height of either a single grid insert 2 or a stack of grid inserts 2 to be accommodated therein. A recessed section 32 is formed in a side wall of frame 3. Recessed section 32 has a size and position allowing the reading of an identification label 28 arranged on grid insert 2 while grid insert 2 is attached to frame 3. By identifying grid insert 2 via the information contained in the identification label 28, the contents of the tubes 4 received in grid insert 2 are known. For example, the information contained in identification label 28 may comprises information about the position of the individual tubes 4 and their contents. Alternatively, identification label 28 may comprise only an identification number of grid insert 2 and the information as to the type of sample and as to the position of a tube containing a respective sample within grid insert 2 is contained in a database, so that upon knowing the identification number of grid insert 2 the remaining information can be retrieved from a database 2. From a technical point of view, identification label 28 may contain machine-readable information such as a bar-code, for example, which may be read by an optical scanner which is connected a processing unit to read identification label 28 and then further process the information contained in identification label 28. Advantageously, tubes 4 which are stored in a grid insert 2 carrying such an identification label 28 are not stored in a fixed position, but rather the position thereof can be tracked and registered (e.g. in a database).

Grid insert 2 comprises a plurality of compartments 21 which subdivide grid insert 2 into a rectangular arrangement of compartments 21. For example, three hundred and eighty-four compartments 21 (sixteen times twenty-four) are formed in grid insert 2. Each compartment 21 is laterally confined by four side walls 22 to form a square through hole for receiving a tube 4. The length of compartment 21 which is defined by grid insert 2 can vary with respect to the number and size of tubes 4 to be stored therein. As an example, one tube 4 can be contained in one compartment 21, however, it is also possible that two tubes 4 each having a length of half the length (depth) of the compartment can be stored longitudinally aligned so as to be stored in the same compartment 21. Alternatively, a single tube 4 can be stored in two mated (longitudinally aligned) compartments of stacked grid inserts 2. Each compartment 21 of the grid insert 2 comprises four side walls 22 which confine a through-hole extending between a top opening and a bottom opening of the through-hole. Through this top opening and bottom opening, respectively, the tube 4 may be moved into and out of the compartment 21. The frame 3 comprises four inner walls 30 laterally confining a through-opening 35 into which the grid insert 2 is inserted from below for getting attached to the frame 3. Once attached to the frame, the grid insert 2 completely closes the through opening 35. The shown attachment of the grid insert 2 to the frame 3 allows for moving tube 4 into and out of each compartment 21 via the respective top opening and bottom opening of the respective compartment 21, since frame 3 does not cover any of the compartments 21 of the attached grid insert 2 but rather allows access to all tubes 4 arranged in the compartments 21 of grid insert 2.

Figure 4:
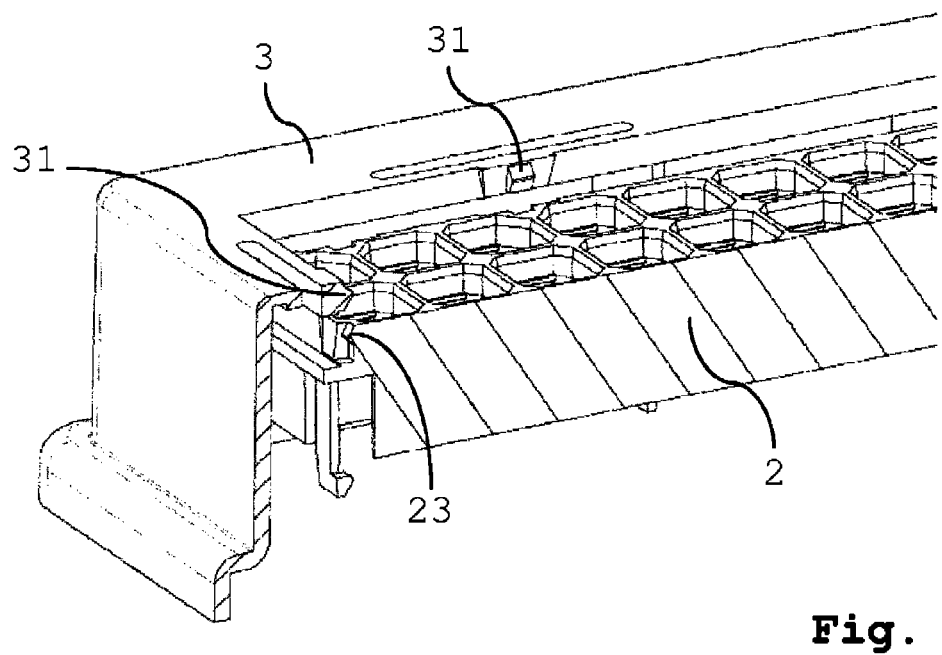
FIG. 4 shows a perspective sectional view of the micro-plate with fastening elements on the frame in an unlocked position (grid insert not yet fixedly attached to the frame)
Figure 5:
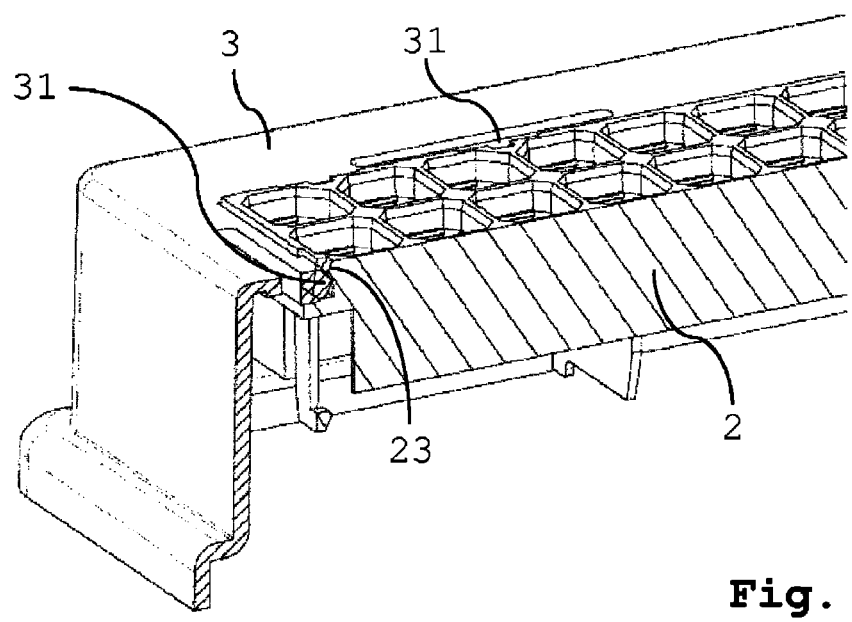
FIG. 5 shows perspective sectional view of the micro-plate of FIG. 4 with the fastening elements on the frame in a locked position (grid insert fixedly attached to the frame)

FIG. 4 and FIG. 5 show sectional views of the micro-plate of FIG. 1 before and after fixedly attaching grid insert 2 to frame 3 to form micro-plate 1. FIG. 4 shows the unlocked position when the grid insert 2 is inserted into frame 3 from below but has not yet been attached thereto. FIG. 5 represents the locked state in which grid insert 2 is fixedly attached to frame 3. As can be seen in FIG. 3, fastening elements 23 are formed on grid insert 2, and corresponding fastening elements 31 are formed on frame 3. The type of fastening elements 23, 31 is not limited to the shown semi-permanent type of fastening, but rather permanent fastening can also be an option in particular when micro-plate 1 is disposed of after use. In the semi-permanent connection of the embodiment shown, grid insert 2 can be attached to frame 3 and can subsequently be detached therefrom again. The fastening elements in this embodiment comprise eight protrusions 31 regularly distributed along the circumference of frame 3, the protrusions 31 being arranged on the inner wall of frame 3. Each protrusion 31 is arranged on a resilient portion of the inner wall of frame 3. The resilient portion is formed by a slot in the inner wall allowing the resilient portion to elastically deform. The resilient portion of the inner wall of frame 3 allows protrusion 31 to move outwardly as the resilient portion of the inner wall of frame 3 deforms upon insertion of grid insert 2 into frame 3 from below. The elasticity of the resilient portion is sufficient to releasably lock grid insert 2 to frame 3 to allow for a save handling of the so formed micro-plate 1. Each protrusion 31 has outer dimensions such that protrusion 31 fits into in a corresponding recess 23 formed on the outer wall of grid insert 2. Each protrusion 31 has an angled surface which is oriented with respect to a upper edge of the grid insert 2 such that as grid insert 2 is inserted into the frame 3 from below protrusion 31 is moved outwardly due to deformation of the resilient portion of the inner wall of frame 3, and subsequently protrusion 31 engages into the corresponding recess 23 formed in grid insert 2, thus releasable locking grid insert 2 to frame 3.

Figure 6:
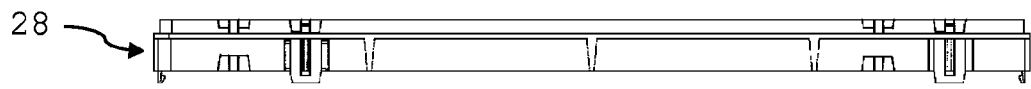
FIG. 6 shows a side view of two grid inserts arranged one above the other but still separated from each other.
Figure 6:
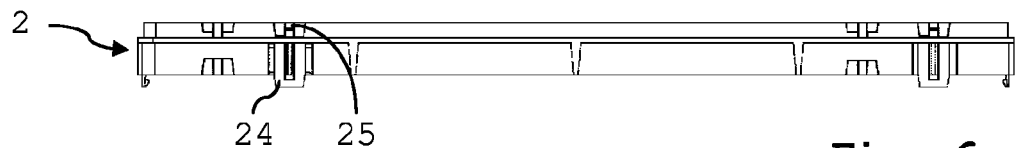
Figure 7:
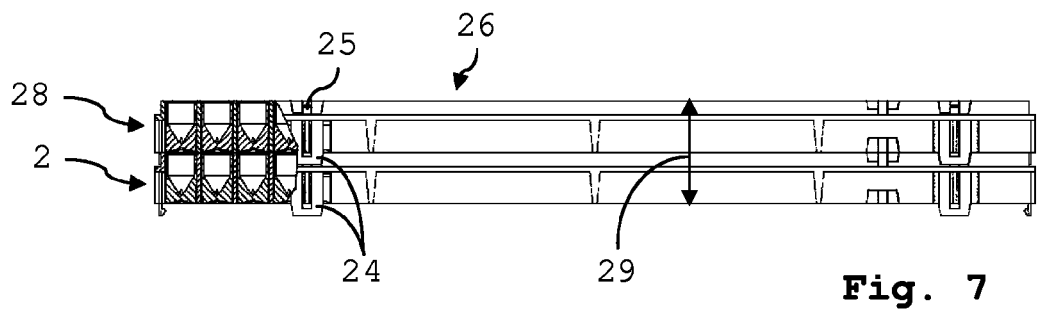
FIG. 7 shows a side view of the two grid inserts of FIG. 6 attached to one another to form a stack of grid inserts.

In FIG. 6 and FIG. 7, a stack 26 of grid inserts (see FIG. 7) is formed by connecting a first individual grid insert 2 and a second individual grid insert 28 (FIG. 6) one above the other to form stack 26. While only two grid inserts 2, 28 are shown for the sake of simplicity, the number of grid inserts is not limited to two such grid inserts, but rather a different number of grid inserts can be stacked one above the other. Stack 26 is formed by connecting first grid insert 2 and second grid insert 28 with the aid of stacking elements in the form of resilient locking member 24 on one hand and notch 25 on the other hand. Grid inserts 2, 28 of stack 26 are connected sufficiently strong to allow handling of stack 26 without the risk of unintended separation of the grid inserts 2, 28. Eight corresponding stacking elements in the form of locking members 24 and corresponding notches 25 connect first grid insert 2 and second grid insert 28 by engagement of the locking members 24 into the corresponding notches 25. Any additional grid insert 28 is connected to stack 26 in the same manner from below. Resilient locking member 24 extends downwardly beyond the respective grid insert 2, 28 so that it gets in contact with the adjacent grid insert 2 arranged immediately below. The elasticity of the resilient locking members 24 is chosen to allow self-locking of the grid inserts by pressing them together.

The grid inserts of stack 26 are arranged to mate with their respective compartments 21 to form joint through-holes, or to say it in other words the compartments 21 of the grid inserts of stack 26 are aligned longitudinally. Accordingly, a tube stored in any of the compartments 21 is movable along such joint-through hole. Also, tubes of a length which is larger than the depth of a single compartment 21 can be stored in such joint-through holes of the grid inserts of stack 26. For example, a tube having a length which is twice the depth of a single compartment 21 can be stored in two adjacently arranged grid inserts of stack 26. To attach stack 26 to frame 3, the uppermost grid insert 28 is attached to the frame 3 with the aid of the fastening elements already described above with reference to FIG. 4 and FIG. 5 by attaching the uppermost grid insert 28 of stack 28 to frame 3.

Figure 8:
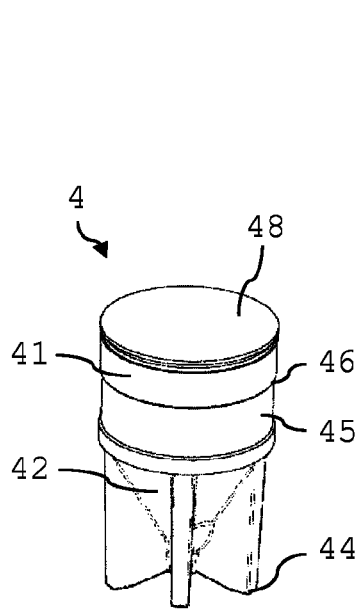
FIG. 8 shows a perspective view of a tube of a sample handling system according to the invention with a small volume.
Figure 9:
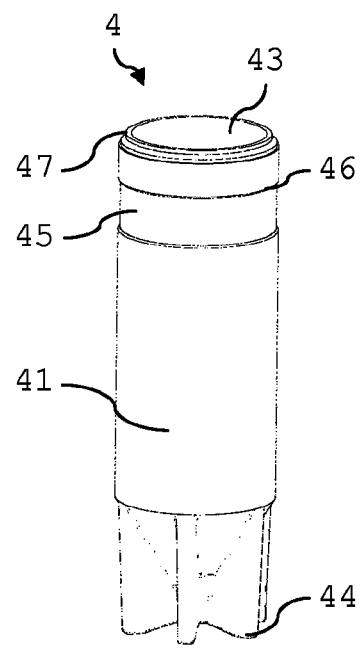
FIG. 9 shows a perspective view of a tube of a sample handling system according to the invention with a large volume.

FIG. 8 shows a tube 4 of a first length which differs from the tube 4 shown in FIG. 9 essentially in the length and, accordingly, in the sample volume which can be stored in the tube 4. Both tubes 4 can be stored in the compartments 21 (see FIG. 3) of the grid insert 2 of micro-plate 1 shown in FIG. 1. Despite the tubes 4 being of different length, they have a very similar outer contour. The tube 4 of smaller volume shown in FIG. 8 has a length such that it can be accommodated inside a single compartment 21 of the grid insert 2 shown in FIG. 3. The tube 4 of the large volume shown in FIG. 9 has a length such that it can be accommodated inside two mated compartments of stacked grid inserts which form a joint through-hole. A plurality of such tubes 4, either of one type or of the other type or of both types, can be stored in a stack formed by two or more than two grid inserts.

Each tube 4 comprises a hollow body 41 with a closed bottom 42. Each tube 4 further comprises an open top 43 (see FIG. 9) which can be closed by sealing a sealing foil 48 (see FIG. 8) to a circumferential rim 47 surrounding the open top of tube 4 after the sample has been filed into tube 4. An abutment portion 44 is formed at the lower end of each tube 4. Abutment portion 44 is capable of abutting against a circumferential rim 47 of a further tube arranged adjacently below in a joint through-hole. Tube 4 further comprises a circumferentially running groove 45 on its outer wall. Groove 45 extends over a certain distance in the axial direction. The upper boundary of the circumferentially running groove 45 is formed by a ledge 46.

Figure 10:
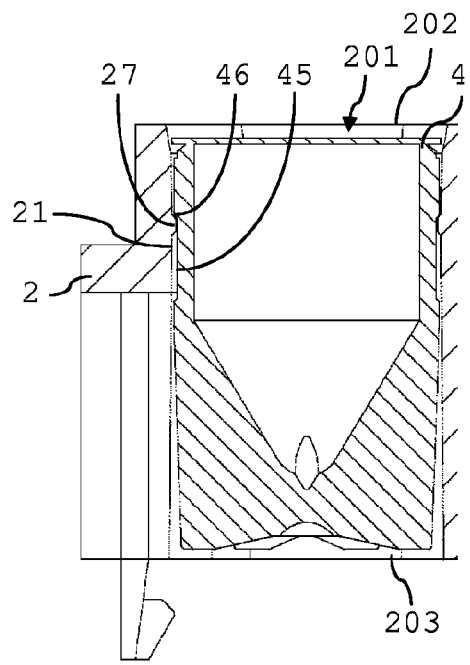
FIG. 10 shows a sectional view of a detail of the grid insert of FIG. 3 with a tube being arranged in the storage position in a compartment of the grid insert.
Figure 11:
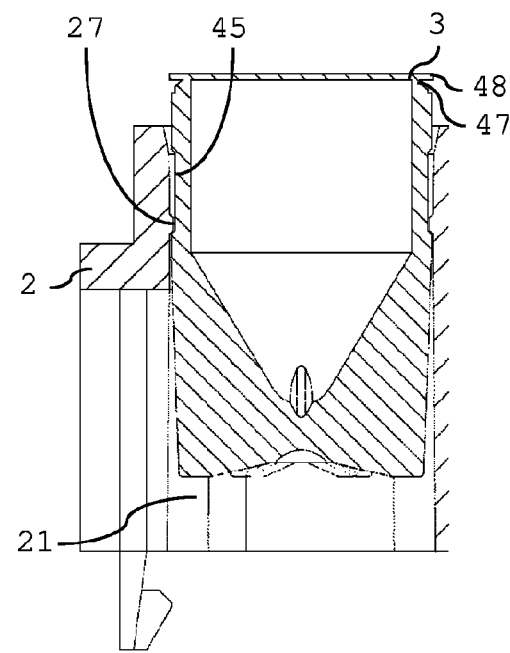
FIG. 11 shows a sectional view of the detail shown in FIG. 10 with the tube being arranged in the sealing position.

Different positions of the tube 4 arranged in the compartment 21 of a grid insert 2 are exemplified by a storage position of the tube 4 as shown in FIG. 10, and a sealing position of the tube 4 as shown in FIG. 11. These different positions are different axial positions of the tube 4 relative to compartment 21 of grid insert 2. In principle, tubes 4 can be inserted into through-hole 201 from above through top opening 202 and from below through bottom opening 203. For example, tubes 4 can be individually punched out of compartment 21 by a punching tool (not shown) which exerts aforce to the top end of tube 4 moving the tube downwards. The tube 4 is further moved downwards along through-hole 201 until it exits compartment 21 via the bottom opening 203. In another example, tubes 4 (elevated by a lifting tool which is not shown) are gripped from above and retrieved by pulling them out of compartment 21 via top opening 202. The different axial positions become evident when glancing at the position of circumferential projection 27 extending inwardly from the side walls of the compartment 21 relative to the circumferentially running groove 45 of tube 4 the upper boundary of which is formed by ledge 46. In both positions, in the sealing position as well as in the storage position, the circumferential projection 27 of the compartment 21 is arranged inside the circumferentially running groove 45 of the tube 4. However, in the storage position (see FIG. 10) the circumferential projection 27 projecting from the inner wall of compartment 21 abuts against ledge 46 such that tube 4 is completely arranged inside compartment 21. By elevating tube 4 with a suitable means tube 4 is pushed into the sealing position (see FIG. 11) in which tube 4 is supported from below (not shown). In the sealing position, circumferential rim 47 of tube 4 is arranged above the upper surface of grid insert 2 such that a sealing foil 48 can be applied to the circumferential rim 47 to close the tube 4 containing the sample. It has already been described above, that in order to obtain individually sealed tubes 4 a sheet of a sealing foil can be placed onto all or a plurality of tubes 4 arranged in the sealing position in the compartments of a grid insert 2. The sheet of sealing foil is then sealed to the rims 47 of the tubes 4 and subsequently the sheet of sealing foil is punched to obtain individually sealed tubes 4 which are then pushed back into the storage position (see FIG. 11).

Figure 12:
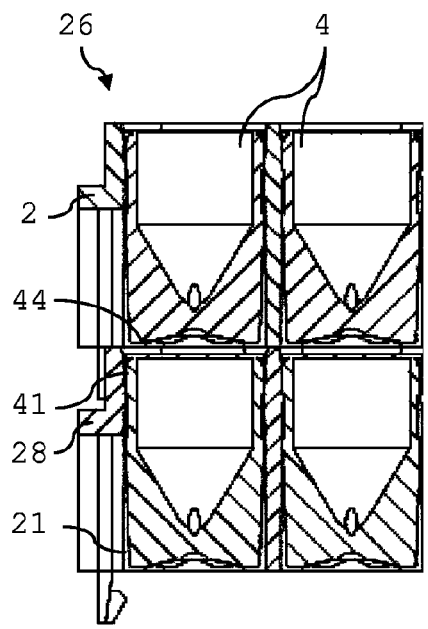
FIG. 12 shows a detail of the stack of grid inserts of FIG. 7 with tubes being arranged the storage position in the grid inserts of the stack
Figure 13:
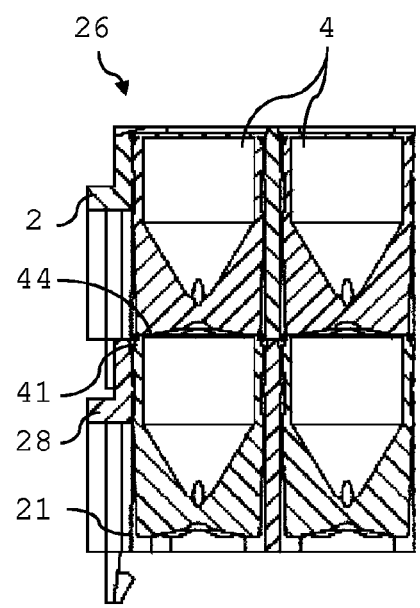
FIG. 13 shows the detail of the stack of grid inserts of FIG. 12 with the tubes of the lowermost grid insert being arranged in a position abutting against the tubes arranged in the storage position in the upper grid insert.

In FIG. 12 and FIG. 13 different arrangements of the tubes in the grid inserts 2, 28 of a stack 26 are shown. In FIG. 12 the tubes 4 are shown arranged completely inside the respective compartment 21 in the storage position. In FIG. 13 the tubes in the lower grid insert 28 have been lifted by a suitable punching means (not shown) into a ready-to-get-punched position (FIG. 13). In the ready-to-get punched position, the tubes of the lower grid insert 28 *h* with their circumferential rims 47 to which the sealing foil is applied are in contact with the abutment portion 44 of the tubes 4 arranged above in the corresponding joint through-hole. In order to punch the tubes 4 arranged in the compartments 21 out of the compartments 21 of upper grid insert 2, the punching means further move the tubes contained in the lower grid insert 28 upwards thereby punching the tubes 4 arranged in the compartments 21 of the upper grid insert 2 out of their compartments 21 into a gripper means (not shown). In case only the tube contained in the uppermost grid insert 2 is the tube of interest, then only this tube is punched into the gripper means. The gripper means then transports this tube to a standard (destination) micro-plate where it is punched from the gripper means into the standard (destination) micro-plate. The standard (destination) micro-plate is loaded with tubes according the needs of the user and is used for further processing after being loaded. In case not only the tube contained in the uppermost grid insert is punched into the gripper means but as many tubes are punched into the gripper means until the lowermost tube in the gripper means is the tube of interest, then the gripper means transports the pile of tubes to the destination standard micro-plate with the tube of interest being the lowermost tube of the pile. The lowermost tube is then punched from the gripper means into the standard (destination) micro-plate while the rest of the tubes are then punched from the gripper means back into the compartments of the grid inserts. If additional tubes of the pile are also of interest, they are also punched into the standard (destination) micro-plate. For the stack 26 comprising first grid insert 2 and second grid insert 28, in case the tube contained in the second grid insert 28 is the tube of interest, then the tube 4 contained in compartment 21 of the first grid insert 2 is first punched into the gripper means by punching the tube contained in second grid insert 28 into compartment 21 of the first grid insert 2, and subsequently also the tube of interest (now contained in compartment 21 of the first grid insert 2) is punched into the gripper means. The gripper means then transports the tubes to the standard (destination) plate where the tube of interest (which is the lowermost tube in the gripper means) is punched into the destination plate. The other tube is then punched out of the gripper means back into compartment 21 of first grid insert 2. Alternatively, if this tube is also of interest then it is also punched into the standard (destination) micro-plate. It goes without saying, that the punching operation can generally be performed in a similar manner in the downward direction as well.

Figure 14:
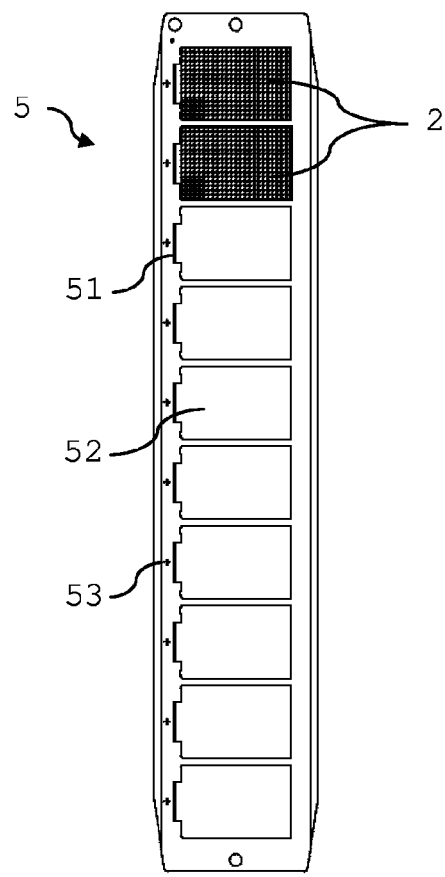
FIG. 14 shows a top view of a tray of a system according to the invention.

FIG. 14 shows a top view of a tray 5 according to the invention which is capable of storing a plurality of grid inserts 2 or stacks 26 of grid inserts in storage compartments 52. In the embodiment shown, the tray 5 comprises ten such storage compartments 52 in which grid inserts 2 or stacks 26 of grind inserts can be stored whereas a tray 5 of the same size is only capable to store eight standard micro-plates (including the frames). A position marker 53 is provided adjacent to each storage compartment 52 to allow a robot to identify the exact position of a grid insert 2 or stack 26 of grid inserts and to automatically pick the respective grid insert 2 or stack 26 of grid inserts from the respective compartment. Also, recesses 51 are provided in the frame of tray 5 to allow for an automatic reading of label 28 (see FIG. 1) of grid insert 2. Trays 5 of this type are typically used to store micro-plates (or in the instant case only grid inserts 2 or stacks 26 of grid inserts) in the freezers of a humidity controlled cold room. The trays 5 can be operated in a drawer-like manner, that is to say after opening the front door of the freezer the respective tray 5 can be pulled out, the desired grid insert 2 or stack 26 can be removed from tray 5, and then tray 5 can be pushed back, so that subsequently the front door of the freezer can be closed again. Alternatively, the entire tray 5 can be pulled out of the freezer, the front door of the freezer can be closed again, and only then the desired grid insert 2 or stack 26 of grid inserts can be picked out of the respective compartment 52 for further processing, whereupon the front door of the freezer can be opened again and tray 5 can be pushed back into the freezer.

Figure 15:
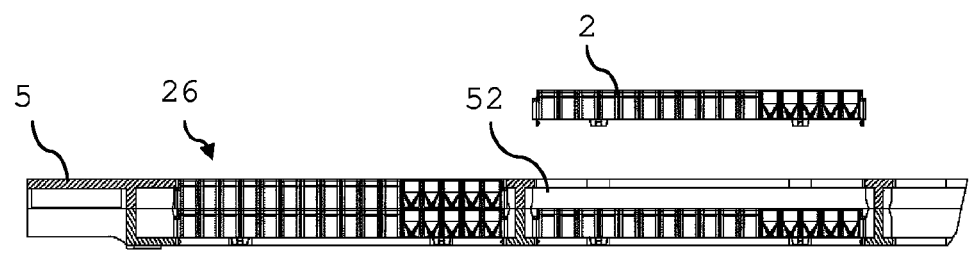
FIG. 15 shows a partial sectional view of the tray of FIG. 14 containing stacks of two grid inserts.

FIG. 15 shows a partial sectional view of tray 5 the compartments 52 of which have a depth which is suitable to accommodate a stack 26 of grid inserts. While in the embodiment shown the compartments 52 are capable of accommodating a stack 26 of only two grid inserts it goes without saying that the compartments may have a depth for accommodating a stack 26 of a higher number of grid inserts. Also, it may be possible to directly retrieve from or reinsert the tubes from the grid insert or the stack of grid inserts when the grid insert or the stack of grid inserts is arranged in compartment 52 of tray 5, thus eliminating the need to pick the grid insert or stack of grid inserts out of the respective compartment 52 for punching. The manner how this retrieving (punching) operation can be performed corresponds to the manner described above. The position marker 53 helps to find the respective compartment in which the tube to be retrieved actually is stored.

Figure 16:
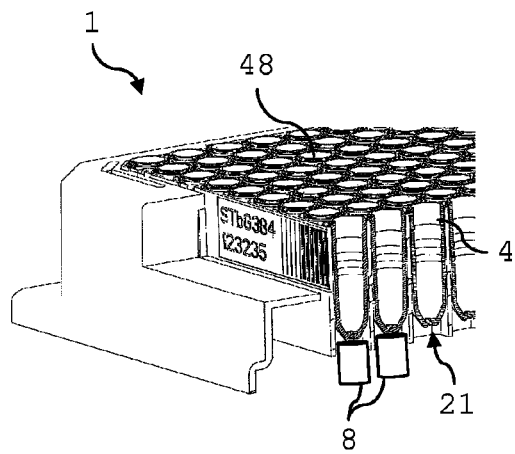
FIG. 16 shows a partial sectional view of a part of the micro-plate of FIG. 1 with tubes being sealed with a sealing foil at their top end used in a method for peeling off the sealing foils.

FIG. 16 shows a sectional view of a part of micro-plate 1 for explaining a further aspect relating to the removal of sealing foils 48 arranged at the top ends of the tubes 4, these sealing foils 48 sealing the tubes 4. The tubes 4 are arranged in compartments 21 in a peeling position which corresponds to the sealing position of the tubes 4 as described in FIG. 11. The tubes 4 are slightly elevated for example by use of a lifting means which may comprise a plurality of pins 8 only two of them being shown. The number of individual pins 8 of the lifting means corresponds to the number of compartments 21 and each pin 8 has a shape and size suitable for allowing them to be introduced into such compartment 21. In FIG. 16, pins 8 are arranged so as to be in contact with the bottom of the tubes 4 to exert an upwardly directed elevating force to the bottom of the tube 4 for moving the tube 4 into the elevated peeling position. Moreover, pins 8 support the tubes 4 in the elevated peeling position. "Peeling" denotes the removal of the sealing foil 48 from the sealed tubes 4 by stripping off the individual sealing foil 48 from the respective rim confining the open end of the respective tube 4. In the peeling position, the top ends of the tubes sealed by the sealing foils are arranged to project upwardly above the top openings of the compartments.

Figure 17:
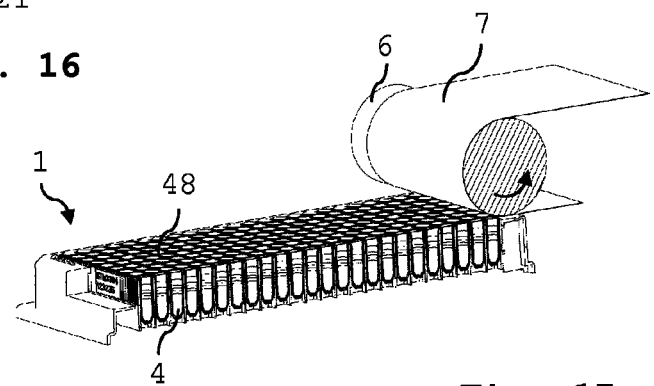
FIG. 17 shows a perspective view of the micro-plate of FIG. 16 in a first step of a method for peeling off the sealing foils.
Figure 18:
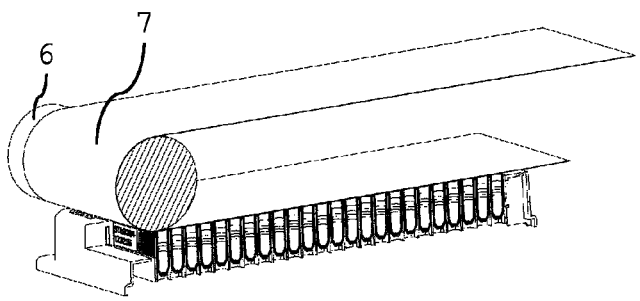
FIG. 18 shows the micro-plate of FIG. 16 at the end of the first step of the method for peeling off the sealing foils.
Figure 19:
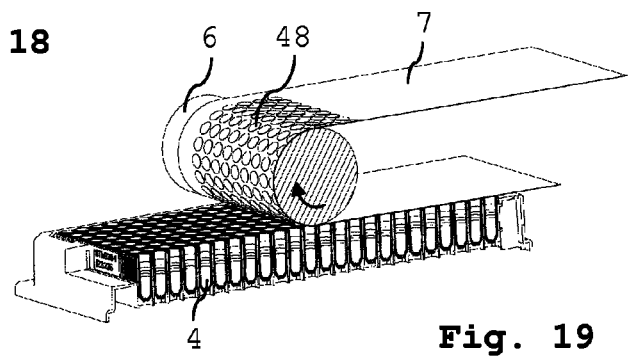
FIG. 19 shows a perspective view of the micro-plate of FIG. 16 in a second step of the method for peeling off the sealing foils.

FIG. 17, FIG. 18 and FIG. 19 show the subsequent steps of a method for peeling off the individual sealing foils from the tubes arranged in the compartments of the micro-plate.

In a first step, illustrated in FIG. 17 and FIG. 18, an adhesive tape 7 is applied to the sealing foils 48 of the tubes 4 arranged in the peeling position. A single strip of adhesive tape 7 is applied to cover all sealing foils 48. The adhesive tape 7 is coated with a layer of adhesive, the adhesive having a tackiness suitable to adhere to the sealing foils 48 so as to allow stripping off the sealing foils 48 by pulling away adhesive tape 7. In the shown example, the adhesive tape 7 is applied with the aid of a roller 6 applying the adhesive tape 7 to the sealing foils 48 by rolling the adhesive tape 7 over the sealing foils 48.

In a second, subsequent step of the method, illustrated in FIG. 19, adhesive tape 7 is pulled away from tubes 4. Again, the roller 6 can be used to pull away the adhesive tape 7. For this purpose, the roller 6 can be moved back (in FIG. 19 to the right). The peeled off sealing foils 48 adhere to the adhesive tape 7, this being partly shown in FIG. 19. This method has the advantage that the individual sealing foils 48 do not need to be removed one by one. After the sealing foils 48 are removed from all tubes 4, the above mentioned lifting means is lowered so as to allow the tubes 4 to slide back into the storage position in the respective compartments (see FIG. 10).

The method for peeling off the individual sealing foils 48 has at least two advantages: Firstly, contamination which may be caused by piercing needles through the sealing foils 48 for retrieving the sample, is prevented. Secondly, the sealing foils 48 are completely removed from the open ends of the tubes 4 so as to allow a proper re-sealing of the tubes after use.

While embodiments of the invention have been described with the aid of the drawings, various modifications and changes to the described embodiments are possible without departing from the general teaching underlying the invention. Therefore, the invention is not to be understood as being limited to the described embodiments, but rather the scope of protection is defined by the appended claims.

The invention claimed is:

1. A sample handling system for handling samples contained in
   tubes, each tube having a hollow body, a closed bottom and an open top for accessing the sample contained in the tube, the system including a micro-plate comprising:
   at least one separate grid insert and at least one further separate grid insert forming a stack of connected grid inserts arranged one above the other in the stack, each of the at least one separate grid insert and the at least one further separate grid insert having a plurality of compartments, each compartment including one or more side walls laterally confining a through-hole, wherein the through-hole has a top opening and a bottom opening and extends between the top opening and the bottom opening, and
   a frame to which only an uppermost one of the at least one separate grid insert and the at least one further separate grid insert of the stack is attached to form the microplate, the frame laterally confining a single through-opening dimensioned to allow for accessing from above each compartment of the uppermost separate grid insert in the stack of connected grid inserts that is attached to the frame and accessing from below each compartment of a lowermost separate grid insert in the stack of connected grid inserts, and to allow for moving a tube into and out of each compartment through each of the top opening and the bottom opening of the through-hole,
   wherein:
   each of the at least one separate grid insert and the at least one further separate grid insert includes one or more stacking elements for connecting the at least one separate grid insert and the at least one further separate grid insert to form the stack of connected grid inserts,
   each stacking element includes at least one resilient locking member extending downwardly beyond a corresponding one of the at least one separate grid insert and the at least one further separate grid insert and further includes at least one notch arranged to lockingly receive the at least one resilient locking member of an above-arranged separate grid insert that is one of the at least one further separate grid insert or the at least one separate grid insert, respectively, and
   each compartment in each of the at least one separate grid insert is longitudinally aligned with a compartment of the at least one further separate grid insert in the stack to form a joint through-hole through which a tube is moveable.

2. A sample handling system according to claim 1, wherein at least one of the frame, the at least one separate grid insert, and the at least one further separate grid insert comprise fastening elements for fixedly attaching the uppermost one of the at least one separate grid insert and the at least one further separate grid insert of the stack to the frame.

3. A sample handling system according to claim 2, wherein the fastening elements for fixedly attaching the uppermost one of the at least one separate grid insert and the at least one further separate grid insert of the stack to the frame comprise one or more protrusions arranged on a resilient portion of the inner wall of the frame and one or more recesses arranged on a portion of the outer wall of the uppermost one of the at least one separate grid insert and the at least one further separate grid insert such that the one or more protrusions lockingly engage with the one or more recesses of the uppermost separate grid insert in the stack of connected grid inserts when the stack is inserted into the frame from below.

4. A sample handling system according to claim 1, wherein the frame has an insertion height greater than or equal to the overall height of the stack.

5. A sample handling system according to claim 1, wherein one or both of the at least one separate grid insert and the at least one further separate grid insert comprise a machine-readable identification label for identifying the at least one separate grid insert or the at least one further separate grid insert and the tubes received in one or both of the at least one separate grid insert and the at least one further separate grid insert.

6. A sample handling system according to claim 5, wherein the frame has a recessed section adjacent to a position of the machine-readable identification label.

7. A sample handling system according to claim 1, wherein each compartment of the at least one separate grid insert or the at least one further separate grid insert comprises a circumferential projection extending inwardly from the one or more side walls confining the through-hole.

8. A sample handling system according to claim 1, wherein the system further comprises tubes, each tube having an abutment portion at the lower end of the tube and a circumferential rim at an open top of the tube, the abutment portion at the lower end of the tube being capable of abutting against the circumferential rim of another tube arranged in the longitudinally aligned compartment of the at least one separate grid insert or the at least one further separate grid insert underneath the tube.

9. A sample handling system according to claim 8, wherein the tube on its outer wall comprises a circumferentially running groove having a width extending in the axial direction and a circumferentially extending ledge which forms the upper boundary of the circumferentially running groove.

10. A sample handling system according to claim 1, wherein the system further comprises a storage tray comprising a plurality of storage compartments, each storage compartment being capable of only accommodating at least one of the at least one separate grid insert and the at least one further separate grid insert of the stack without the frame, which is separable from the uppermost one of the at least one separate grid insert and the at least one further separate grid insert of the stack.

11. A sample handling system according to claim 10, wherein the storage compartments of the storage tray have a depth such that they are capable of accommodating all separate grid inserts of the stack of connected grid inserts.

12. A sample handling system according to claim 10, wherein the tray comprises position markers thereon at locations of the storage compartments for indicating a position of the at least one separate grid insert or the at least one further separate grid insert.

13. A sample handling system according to claim 11, wherein the storage tray comprises position markers thereon at locations of the storage compartments for indicating the position of all separate grid inserts of the stack of connected grid inserts.

14. A sample handling system according to claim 1, wherein the system further comprises tubes of different lengths accommodated in the plurality of compartments, wherein the respective longitudinally aligned compartments forming the joint through-holes are configured such that each tube of the tubes of different lengths is completely immersed within the stack of connected grid inserts.

* * * * *